United States Patent
Li et al.

(10) Patent No.: US 8,812,102 B2
(45) Date of Patent: Aug. 19, 2014

(54) SENSOR RESPONSE DELAY FOR HEMODYNAMIC STABILITY DETECTION DURING ARRHYTHMIA

(75) Inventors: Dan Li, Shoreview, MN (US); Amy Jean Brisben, Saint Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 31 days.

(21) Appl. No.: 13/467,695

(22) Filed: May 9, 2012

(65) Prior Publication Data

US 2012/0303078 A1 Nov. 29, 2012

Related U.S. Application Data

(60) Provisional application No. 61/488,872, filed on May 23, 2011.

(51) Int. Cl.
*A61N 1/39* (2006.01)
*A61N 1/365* (2006.01)

(52) U.S. Cl.
USPC ........ 607/4; 607/5; 607/14; 607/15; 600/509; 600/515; 600/517; 600/518

(58) Field of Classification Search
USPC ......... 600/509, 515, 517, 518; 607/4, 5, 6, 14
See application file for complete search history.

(56) References Cited

U.S. PATENT DOCUMENTS

| | | | |
|---|---|---|---|
| 4,895,151 A * | 1/1990 | Grevis et al. ..................... 607/4 |
| 5,179,946 A * | 1/1993 | Weiss ................................ 607/4 |
| 5,184,614 A * | 2/1993 | Collins et al. ................. 607/107 |
| 5,480,412 A | 1/1996 | Mouchawar et al. |
| 5,549,650 A | 8/1996 | Bornzin et al. |
| 5,554,174 A * | 9/1996 | Causey, III ....................... 607/5 |
| 6,009,349 A | 12/1999 | Mouchawar et al. |
| 6,058,328 A * | 5/2000 | Levine et al. .................. 607/14 |
| 6,477,406 B1 | 11/2002 | Turcott |
| 6,666,826 B2 | 12/2003 | Salo et al. |
| 6,792,308 B2 | 9/2004 | Corbucci |
| 6,937,899 B2 | 8/2005 | Sheldon et al. |
| 7,079,896 B1 | 7/2006 | Park et al. |
| 7,181,268 B2 | 2/2007 | Sheldon et al. |
| 7,225,017 B1 * | 5/2007 | Shelchuk ......................... 607/4 |
| 7,299,086 B2 | 11/2007 | McCabe et al. |
| 7,972,275 B2 | 7/2011 | Siejko et al. |
| 8,239,011 B2 * | 8/2012 | Li ................................. 600/518 |
| 8,617,082 B2 * | 12/2013 | Zhang et al. .................. 600/528 |
| 2004/0049235 A1 * | 3/2004 | Deno et al. ........................ 607/9 |
| 2004/0127792 A1 | 7/2004 | Siejko et al. |
| 2004/0220631 A1 * | 11/2004 | Burnes et al. ..................... 607/9 |
| 2005/0115561 A1 * | 6/2005 | Stahmann et al. ....... 128/200.24 |

(Continued)

*Primary Examiner* — Niketa Patel
*Assistant Examiner* — Christopher A Flory
(74) *Attorney, Agent, or Firm* — Schwegman, Lundberg & Woessner, P.A.

(57) ABSTRACT

An apparatus comprises a cardiac signal sensing circuit, a physiologic sensor circuit configured to provide a physiologic sensor signal representative of mechanical cardiac activity, a therapy circuit, and a control circuit. The control circuit includes a cardiac depolarization detection circuit, a tachyarrhythmia detection circuit, and a timer circuit. A time interval between a mechanical cardiac event and a detected fiducial electrical cardiac event is monitored. The control circuit is configured to correct the monitored time interval for variation with heart rate to form a corrected electromechanical time interval, initiate anti-tachyarrhythmia therapy when the corrected electromechanical time interval satisfies a specified time interval threshold value during a detected episode of tachyarrhythmia, and withhold anti-tachyarrhythmia therapy otherwise.

10 Claims, 7 Drawing Sheets

(56) References Cited

U.S. PATENT DOCUMENTS

| | | | |
|---|---|---|---|
| 2005/0177135 A1* | 8/2005 | Hildebrand et al. | 604/890.1 |
| 2006/0247702 A1* | 11/2006 | Stegemann et al. | 607/17 |
| 2006/0293714 A1 | 12/2006 | Salo et al. | |
| 2007/0179390 A1* | 8/2007 | Schecter | 600/508 |
| 2007/0191901 A1* | 8/2007 | Schecter | 607/17 |
| 2007/0239218 A1 | 10/2007 | Carlson et al. | |
| 2007/0249945 A1* | 10/2007 | Li et al. | 600/515 |
| 2007/0299477 A1* | 12/2007 | Kleckner et al. | 607/9 |
| 2008/0287818 A1* | 11/2008 | Shelchuk et al. | 600/509 |
| 2009/0204163 A1 | 8/2009 | Shuros et al. | |
| 2009/0287106 A1 | 11/2009 | Zhang et al. | |
| 2010/0023081 A1* | 1/2010 | Audet et al. | 607/18 |
| 2010/0106213 A1* | 4/2010 | Hilpisch et al. | 607/23 |
| 2010/0152804 A1* | 6/2010 | Kleckner et al. | 607/17 |
| 2010/0198291 A1* | 8/2010 | Sambelashvili et al. | 607/17 |
| 2011/0105927 A1* | 5/2011 | Greenhut et al. | 600/513 |
| 2011/0160790 A1* | 6/2011 | Stegemann et al. | 607/18 |
| 2012/0065528 A1* | 3/2012 | Gill et al. | 600/509 |
| 2012/0296228 A1* | 11/2012 | Zhang et al. | 600/513 |
| 2012/0303084 A1* | 11/2012 | Kleckner et al. | 607/25 |

* cited by examiner

SENSOR RESPONSE DELAY FOR HEMODYNAMIC STABILITY DETECTION DURING ARRHYTHMIA

CLAIM OF PRIORITY

This application claims the benefit of priority under 35 U.S.C. §119(e) of Li et al., U.S. Provisional Patent Application Ser. No. 61/488,872, entitled "SENSOR RESPONSE DELAY FOR HEMODYNAMIC STABILITY DETECTION DURING ARRHYTHMIA", filed on May 23, 2011, which is herein incorporated by reference in its entirety.

BACKGROUND

Ambulatory medical devices include implantable medical devices (IMDs) and wearable medical devices (WMDs). Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

WMDs include wearable cardioverter defibrillators (WCDs) and wearable diagnostic devices (e.g., an ambulatory monitoring vest). WCDs can be monitoring devices that include surface electrodes. The surface electrodes are arranged to provide one or both of monitoring to provide surface electrocardiograms (ECGs) and delivering cardioverter and defibrillator shock therapy.

Some medical devices detect events by monitoring electrical heart activity signals. In CFM devices, these events can include electrical cardiac activity. By monitoring cardiac electrical signals, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, tachyarrhythmia can be terminated with high energy shock therapy using an ICD or WCD. Under-detection of tachyarrhythmia (i.e., the device does not recognize an episode of tachyarrhythmia) may leave tachyarrhythmia untreated. Additionally, over-detection of tachyarrhythmia by a device (i.e., the IMD categorizes too many false-positives as tachyarrhythmia) is undesirable for the patient and the device. Cardioversion/defibrillation therapy can cause patient discomfort and consumes a relatively large amount of battery power which may lead to a shortened useful device lifetime. Therefore, it is important to accurately detect tachyarrhythmia.

OVERVIEW

Systems and methods for performing rhythm discrimination that includes confirming the type of event based on the mechanical and electrical activity signals are described in U.S. Patent Application Serial No. 2009/0204163, filed Feb. 5, 2009. A description of devices and methods for therapy control based on electromechanical timing can be found in U.S. Patent Application Serial No. 2006/0293714, filed Jun. 28, 2005.

This document relates generally to systems, devices, and methods that provide electrical pacing therapy to the heart of a patient or subject. In particular it relates to systems, devices, and methods that determine the decision making process for whether to deliver anti-tachyarrhythmia therapy and, if so, when to deliver therapy and what type of therapy to deliver (e.g., anti-tachyarrhythmia pacing (ATP) or defibrillation shock therapy).

An apparatus example can include a cardiac signal sensing circuit configured to provide a cardiac signal representative of electrical cardiac activity, a physiologic sensor circuit configured to provide a physiologic sensor signal representative of mechanical cardiac activity, a therapy circuit configured to provide anti-tachyarrhythmia therapy, and a control circuit. The control circuit can include a cardiac depolarization detection circuit configured to detect a cardiac depolarization using at least one of the cardiac signal and the physiologic sensor signal, a tachyarrhythmia detection circuit, and a timer circuit configured to monitor a time interval between a mechanical cardiac event and a detected fiducial electrical cardiac event. The control circuit can be configured to correct the monitored time interval for variation with heart rate to form a corrected electromechanical time interval, initiate anti-tachyarrhythmia therapy when the corrected electromechanical time interval satisfies a specified time interval threshold value during a detected episode of tachyarrhythmia, and withhold anti-tachyarrhythmia therapy otherwise.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

This document discusses systems and methods for improved detection of tachyarrhythmia for a patient or subject. Contractility of one or both of the right and left ventricles can deteriorate during VT. This deterioration in contractility can be reflected in the performance of the patient's hemodynamic system. For example, the change in contractility may prevent the heart chambers from filling properly; resulting in a drop in a patient's blood pressure. In some types of tachyarrhythmia (e.g., SVT), the heart rate becomes rapid but a patient's hemodynamic system remains stable. This is because the heart rate may remain regular enough so that the heart chambers are able to fill adequately and contract adequately to maintain adequate blood pressure. A proper assessment of contractility is useful in making a decision in whether to deliver or to delay treatment of a detected tachyarrhythmia.

Figure 1:
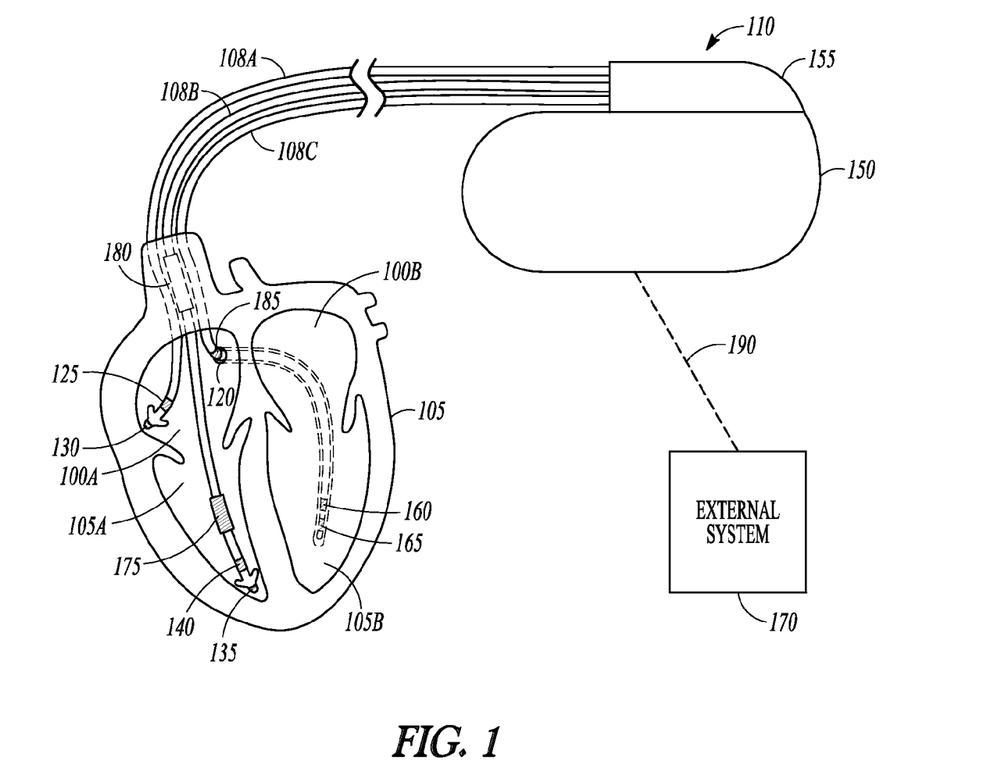
FIG. 1 is an illustration of an example of portions of a system that includes an IMD.

FIG. 1 is an illustration of portions of a system that uses an IMD 110. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles. The IMD 110 can include a third cardiac lead 108C attached to the IMD 110 through the header 155. The third cardiac lead 108C includes electrodes 160 and 165 placed in a coronary vein lying epicardially on the left ventricle (LV) 105B via the coronary vein, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
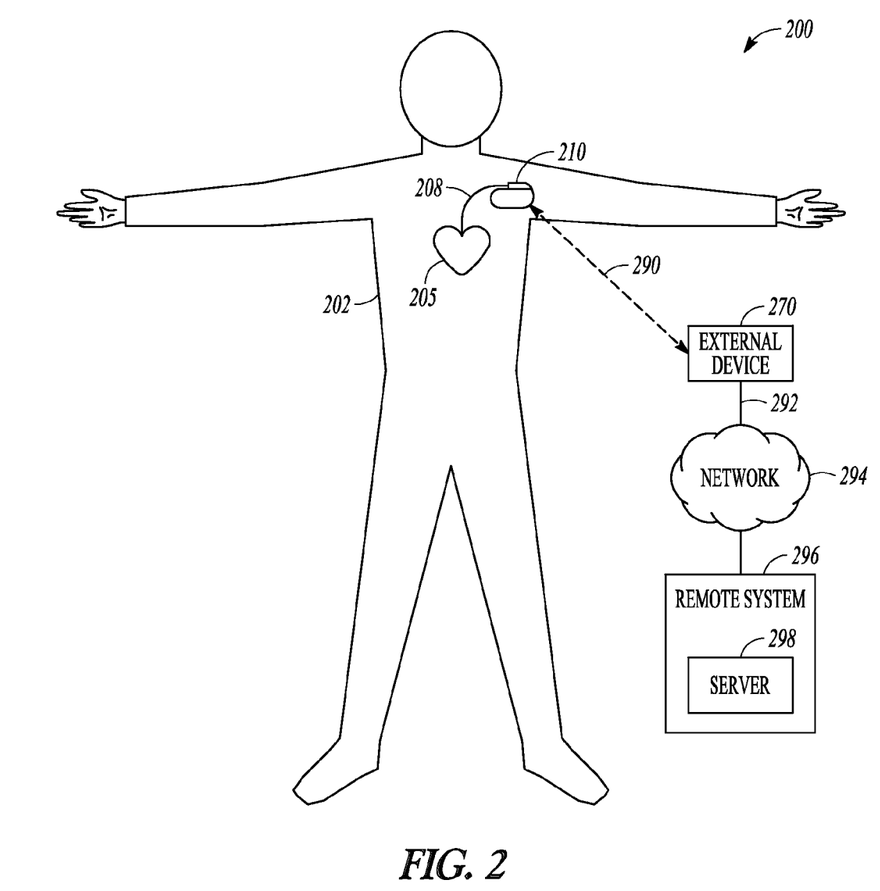
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates wireless signals 290 with the IMD. The external device 270 also communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

Figure 3:
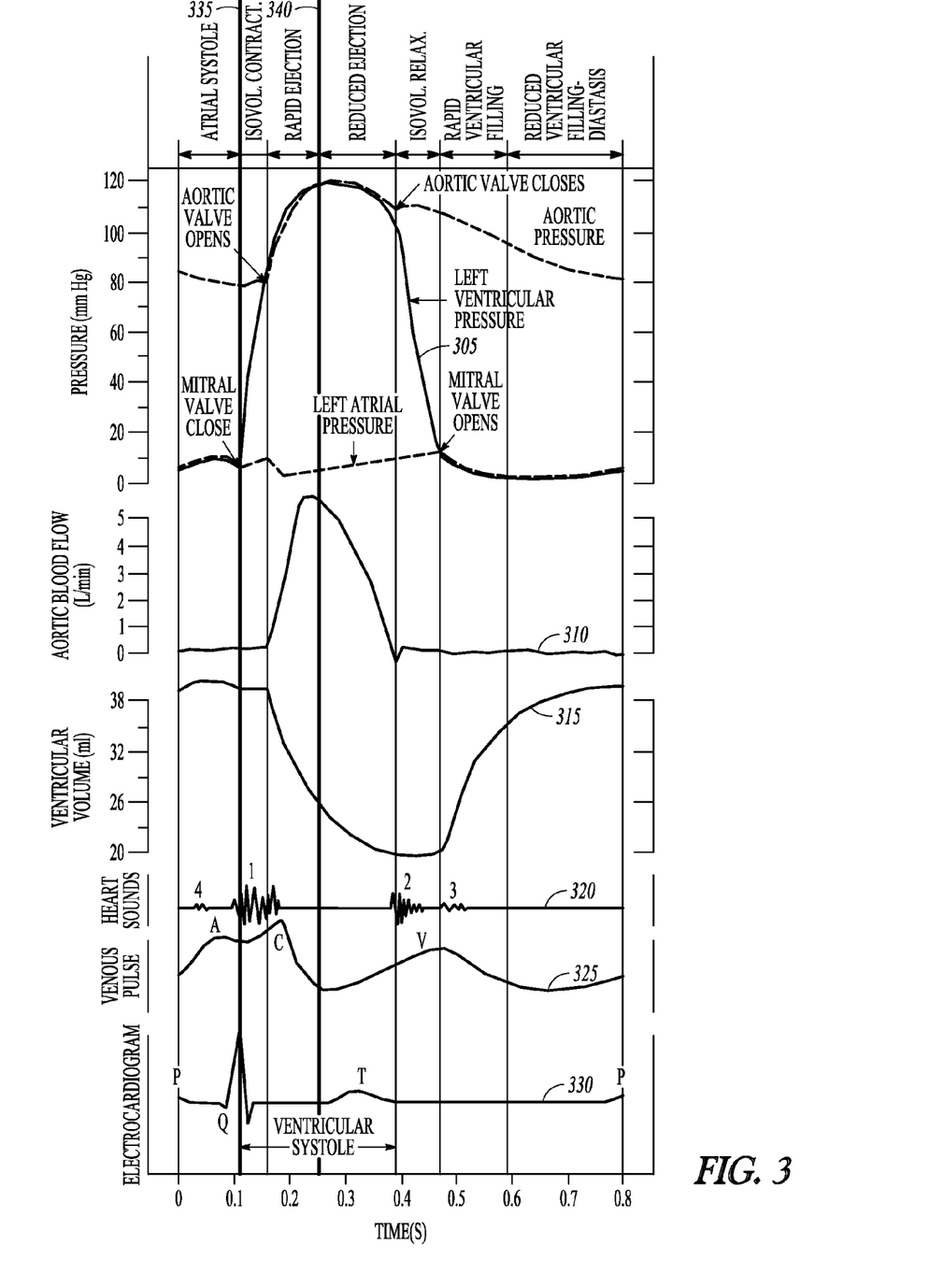
FIG. 3 is an illustration of relative timing of electrical and mechanical cardiac events.

As explained previously, assessment of mechanical contractility of the heart can be useful in making a decision in whether to deliver or to delay treatment of a detected tachyarrhythmia. Changes in contractility can be detected in changes in the systemic hemodynamics of the patient. FIG. 3 is an illustration of relative timing of electrical and mechanical cardiac events. Included in the Figure are cardiac cycle representations of left ventricular pressure 305, aortic blood flow 310, ventricular volume 315, heart sounds 320, venous pulse 325, and a representation of a PQRST complex 330 of an electrocardiogram (ECG).

Deterioration of contractility with VT can be reflected in changes in the timing of the events. Two vertical lines 335 and 340 are shown in the Figure. The first vertical line 335 corresponds to the beginning of an isovolumetric or isovolumic contraction during a heartbeat. The Figure shows that the contraction begins with the closing of the mitral valve and is followed by a rapid increase in left ventricular pressure. The isovolumetric contraction ends when the aortic valve opens and rapid ejection of blood from the ventricles begins. The second vertical line 340 corresponds to the end of the time of rapid ejection of blood from the ventricles. The time of isovolumetric contraction and the time of rapid ejection may co-vary with changes in contractility and changes in relaxation during tachyarrhythmia.

The Figure also shows that the combined time intervals of isovolumetric contraction and rapid ejection approximately correspond to the time between the electrical R-wave of a depolarization (where vertical line 335 intersects PQRST complex 330) and the peak left ventricular systolic pressure (LVSP, where vertical line 340 intersects the curve of left ventricular pressure 305). This R-LVSP interval also may vary during tachyarrhythmia. Thus, the example shows that monitoring the time interval between a reference fiducial in an electrical cardiac signal (e.g., an R-wave) and a mechanical event (e.g., LVSP) may be useful to detect changes in systemic hemodynamics of the patient during tachyarrhythmia. These types of intervals can be referred to as electromechanical time intervals or EMT intervals. It should be noted that the electrical fiducial is related to electrical cardiac activity that is different from an electrical stimulation by the medical device. A time period from electrical stimulation to contraction of myocardial tissue is typically referred to as an electromechanical delay. Monitoring the EMT intervals with a medical device can provide information used to determine whether to deliver or to delay treatment, or to determine which treatment to use.

Figure 4:
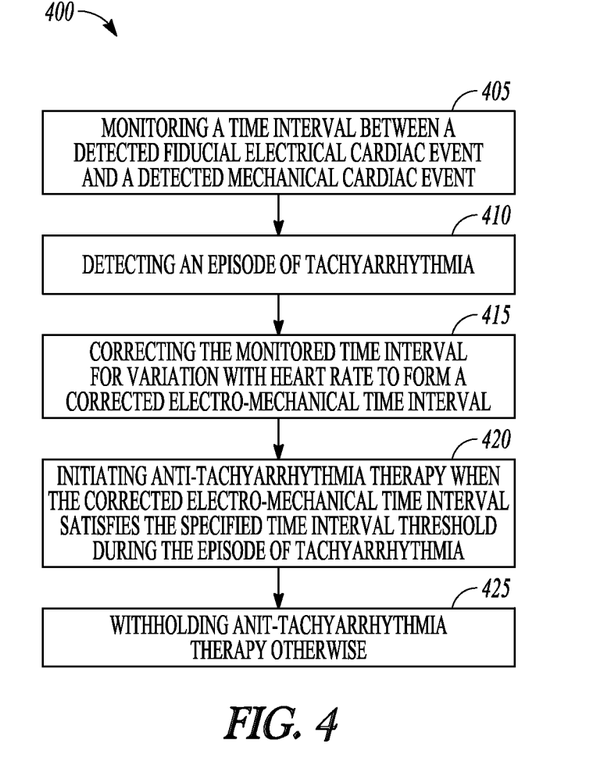
FIG. 4 is a flow diagram of an example of a method of operating a medical device.

FIG. 4 is a flow diagram of an example of a method 400 of operating a medical device. At block 405, a time interval between a detected fiducial electrical cardiac event and a detected mechanical cardiac event is monitored. The electromechanical interval can be an EMT interval. In some examples, the electrical event is detected from a surface electrocardiograph (ECG) signal. In some examples, the electrical event is detected from an electrogram signal. The fiducial in the electrical signal may be a signal maximum, a signal minimum, a point of signal inflection, or other fiducial. The mechanical cardiac event may be detected from cardiac pressure, cardiac impedance, or a heart sound. Some examples of a mechanical event include a fiducial (e.g., a peak) in sensed cardiac pressure, sensed cardiac impedance, or a fiducial in a sensed heart sound.

At block 410, an episode of tachyarrhythmia is detected by the medical device. In some examples, the episode is detected when a heart rate is detected that exceeds a tachyarrhythmia detection threshold rate. In some examples, the episode is detected when detecting a sustained cardiac depolarization interval that is less than a tachyarrhythmia detection interval threshold.

At block 415, the monitored electromechanical time interval is corrected with heart rate to form a corrected electromechanical time interval. A time interval delay may change with heart rate. Using a corrected time interval allows detection of changes in systemic hemodynamics irrespective of heart rate. In some examples, the electromechanical time interval is corrected by normalizing the interval with a measured heart rate or a measured heart beat interval. In certain examples, the monitored time interval (e.g., EMT) is corrected using a ratio that includes the measured heart rate interval (e.g., R-wave to R-wave interval or RR), such as $EMT_C=EMT/RR$.

In certain examples, a baseline electromechanical time interval (e.g., $EMT_{BL}$) is established during normal sinus rhythm (NSR). The electromechanical time interval is corrected by normalizing the value of the electromechanical time interval measured during the episode of tachyarrhythmia with the baseline electromechanical time interval, such as $EMT_C=EMT/EMT_{BL}$.

At block 420, anti-tachyarrhythmia therapy is initiated by the medical device when the corrected electromechanical time interval satisfies the specified time interval threshold value during the episode of tachyarrhythmia, and at block 425 anti-tachyarrhythmia therapy is withheld otherwise.

The threshold value can be determined from mapping the monitored interval to hemodynamic performance of a patient. An example can be shown using the graph in FIG. 5 that shows three clinically induced tachyarrhythmia episodes from different patients. The graph maps mean arterial pressure (MAP) to the electromechanical time interval measured from an R-wave peak to a peak of RV systolic pressure (R-RVSP delay). Each episode is represented by a straight line. The straight lines are a least square fit through the points of data, and the points of data represent averages of the measured data over five seconds of time. The graphs show that R-RVSP delay decreases with the decrease in MAP, which shows that R-RVSP delay can be used as a surrogate to monitor MAP.

Figure 5:
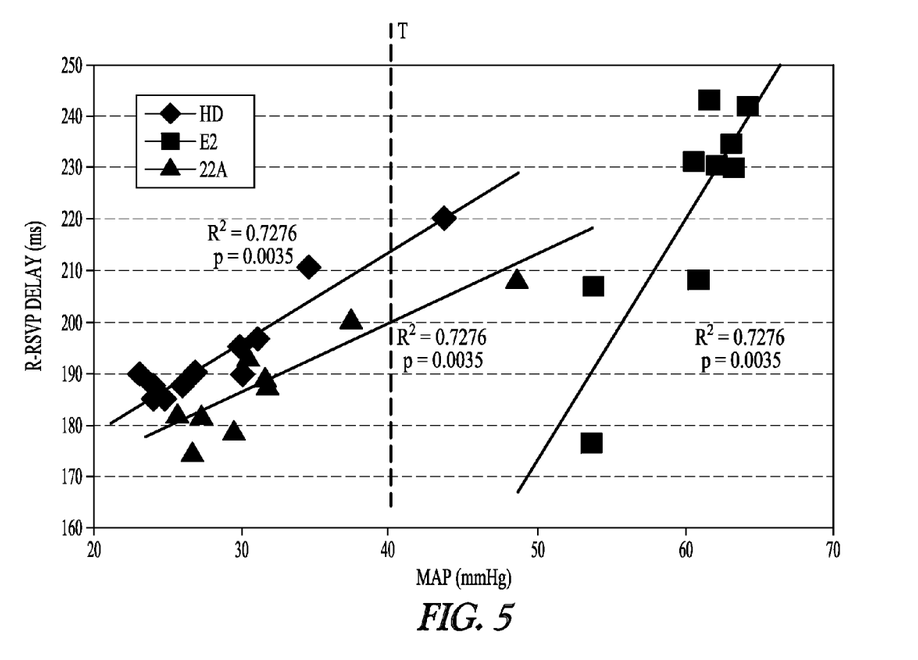
FIG. 5 shows a graph useful for showing an example of determining a threshold value for an electromechanical time interval.

To determine a threshold value for the interval, a physician or other caregiver could decide that therapy should be delivered when the subject's MAP declined to 40 mmHg. Based on this MAP threshold, the physician may specify the interval threshold to be about 210 ms to ensure that MAP does not decrease lower than 40 mmHg. Hence, the medical device would initiate therapy when the measured RVSP delay decreases to 210 ms. The threshold value can be determined using data from a patient or using data from a patient population.

Figure 6:
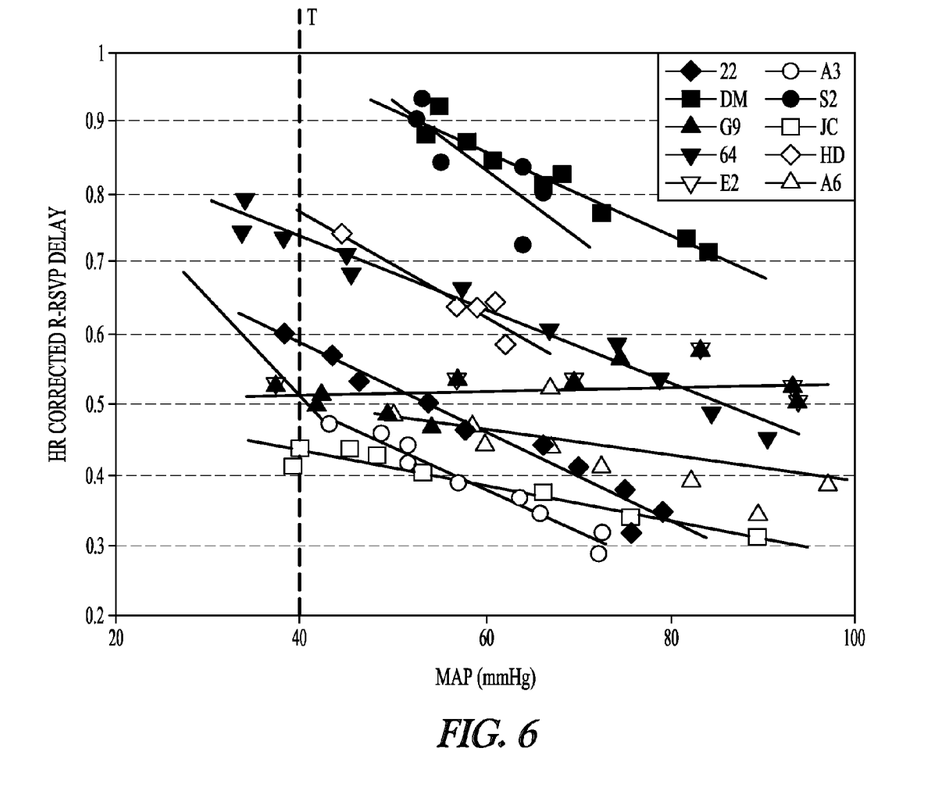
FIG. 6 is used to show another example of determining a threshold value for an electromechanical time interval.

FIG. 6 shows a graph of another example of determining a threshold value for an electromechanical time interval. The graph shows several examples of simulated tachyarrhythmia episodes during right ventricular pacing at different rates, and maps mean arterial pressure (MAP) to a corrected delay interval from an R-wave peak to a peak of RV systolic pressure (R-RVSP delay). The delay is normalized for heart rate. If a physician again decides that therapy should be delivered when the subject's MAP declined to 40 mmHg, then the physician may specify the corrected time interval threshold value to be about 0.45. Anti-tachyarrhythmia therapy can be initiated when the corrected RVSP delay rises above 0.45.

Figure 7:
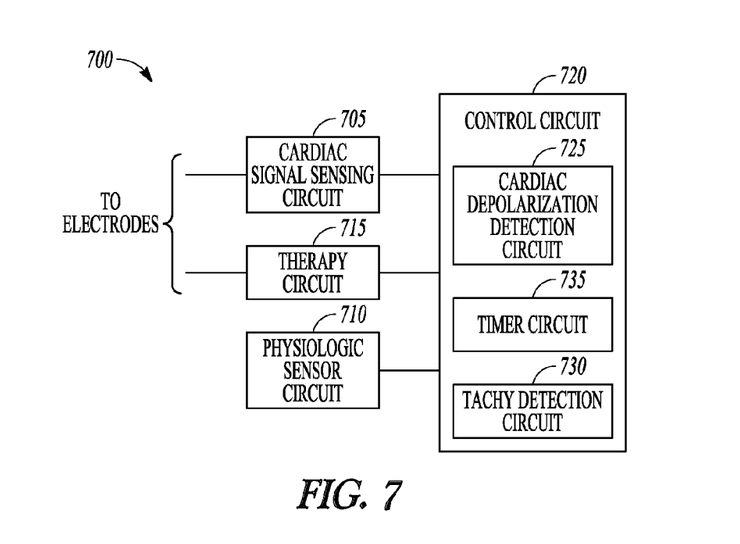
FIG. 7 is a block diagram of portions of an example of a device that provides anti-tachyarrhythmia therapy.

FIG. 7 is a block diagram of portions of an example of a device 700 that provides anti-tachyarrhythmia therapy. The device 700 includes a cardiac signal sensing circuit 705, a physiologic sensor circuit 710, and a therapy circuit 715.

The cardiac signal sensing circuit 705 is configured to provide a cardiac signal representative of electrical cardiac activity. In some examples the device 700 is wearable and the cardiac signal sensing circuit 705 includes a surface (e.g., skin contact) ECG circuit to sense the cardiac signal. In some examples the device 700 is implantable and the cardiac signal sensing circuit 705 includes implantable electrodes, a sense amplifier and a sampling circuit to sense an electrogram signal. In some examples, cardiac signal sensing circuit 705 includes a wireless ECG circuit. A wireless ECG is a signal approximating the surface ECG and is acquired without using surface electrodes. An example of a circuit for sensing the wireless ECG is discussed in commonly assigned, co-pending U.S. Pat. No. 7,299,086, entitled "WIRELESS ECG IN IMPLANTABLE DEVICES," filed on Mar. 5, 2004, which is incorporated herein by reference in its entirety.

The physiologic sensor circuit 710 is configured to provide a physiologic sensor signal representative of mechanical cardiac activity. In some examples, the physiologic sensor circuit 710 includes a pressure sensor configured (e.g., by shape and size) for location at or near the LV and the physiologic sensor signal is representative of LV chamber pressure. In an example, a pressure sensor is implanted in a coronary vessel to determine left ventricle pressure by direct measurement of coronary vessel pressure. A description of systems and methods that use such an implantable pressure sensor is found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference in its entirety. Other cardiac pressure sensors examples include a right ventricle (RV) chamber pressure sensor and a pulmonary artery (PA) pressure sensor, which provide a physiologic sensor signal representative of RV and PA pressure respectively.

In some examples, the physiologic sensor circuit 710 includes a cardiac impedance sensing circuit. A cardiac impedance sensing circuit senses an electrical impedance signal between electrodes interposed in the heart. For the example shown in FIG. 1, a cardiac impedance sensor can provide a physiologic signal representative of intracardiac impedance of the right ventricle 105A by sensing impedance between an electrode placed at the apex of the right ventricle 105A (e.g., electrode 135) and an electrode placed in the right atrium 100A (e.g., electrode 130). A predetermined excitation current is delivered between the electrodes and a voltage is sensed between the same or different electrodes. The cardiac impedance can be determined by the medical device using Ohm's Law (R=V/I). A cardiac impedance signal can also provide a physiologic signal representative of transthoracic impedance by sensing impedance between ring electrode 140 and an electrode formed on the device can 150 or header 155. In some examples, the cardiac impedance sensing circuit senses impedance between surface electrodes of a wearable device.

In some examples, the physiologic sensor circuit 710 includes a heart sound sensing circuit. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

A heart sound sensing circuit produces a physiologic signal which is representative of mechanical activity of a patient's heart and includes representations of one or more heart sounds. Examples of sensors used to detect heart sounds include accelerometers and microphones. A description of circuits for monitoring heart sounds is found in U.S. patent application Ser. No. 10/334,694, entitled "METHOD AND APPARATUS FOR MONITORING OF DIASTOLIC HEMODYNAMICS," filed on Dec. 30, 2002, which is incorporated herein by reference in its entirety.

The therapy circuit 715 is configured to provide anti-tachyarrhythmia therapy. In some examples, the therapy circuit 715 delivers high energy cardioversion and/or defibrillation shock therapy to the heart. In some examples, the therapy circuit 715 delivers anti-tachyarrhythmia pacing (ATP) therapy to the heart. In some examples, the therapy circuit 715 selectively delivers electrical cardioversion/defibrillation shock therapy and electrical pacing stimulation energy to the heart.

The device 700 also includes a control circuit 720 communicatively coupled to the cardiac signal sensing circuit 705, the physiologic sensor circuit 710, and the therapy circuit 715. The communicative coupling allows the control circuit 720 to communicate electrical signals with one or more of the cardiac signal sensing circuit 705, the physiologic sensor circuit 710, and the therapy circuit 715 even though there may be intervening circuitry. The control circuit 720 can be a processor, a digital signal processor, application specific integrated circuit (ASIC), microprocessor, or other type of processor, interpreting or executing instructions in software modules or firmware modules. The control circuit 720 can include other circuits or sub-circuits to perform the functions described. These circuits may include software, hardware, firmware or any combination thereof. Multiple functions can be performed in one or more of the circuits as desired.

The control circuit 720 includes a cardiac depolarization detection circuit 725 configured to detect a cardiac depolarization using at least one of the cardiac signal and the physiologic sensor signal. In some examples, the cardiac depolarization detection circuit 725 detects cardiac depolarization from a fiducial (e.g., an R-wave peak) in an electrogram or ECG signal. In some examples, the cardiac depolarization detection circuit 725 detects cardiac depolarization using a cardiac impedance signal, pressure signal, or heart sound signal. Cardiac impedance and pressure are responsive to cardiac contractions and cardiac depolarization interval or rate can be determined from swings in a cardiac impedance signal or pressure signal that occur with each cardiac contraction. Depolarization interval or rate can be determined by detecting a heart sound (e.g., S1 or S2) in a heart sound signal.

The control circuit 720 also includes a tachyarrhythmia detection circuit 730. In some examples, the tachyarrhythmia detection circuit 730 detects tachyarrhythmia when a detected cardiac depolarization rate or interval satisfies a specified rate or interval detection threshold value. In some examples, the rate or interval has to be sustained for a specified minimum amount of time or cardiac cycles before tachyarrhythmia is declared by the device 700.

The control circuit 720 also includes a timer circuit 735 configured to monitor a time interval between a mechanical cardiac event and a detected fiducial electrical cardiac event. The mechanical cardiac event can include a fiducial in the physiologic signal. As explained previously, a non-exhaustive list of examples of such a fiducial include a maximum (e.g., a peak) in the signal, a minimum in the signal, or a point of inflection in the signal. Some examples of the time interval include a time interval from an R-wave peak in a QRS complex of a cardiac signal to a peak in RV systolic pressure (R-RVSP delay), a time interval from an R-wave peak to a peak in cardiac impedance (R-Z delay), and a time interval from an R-wave peak to a fiducial or measurement in a detected heart sound (R-HS delay). Monitoring the delay provides a measure of hemodynamic stability of the patient during a detected episode of tachyarrhythmia.

The control circuit 720 is configured to correct the monitored time interval for variation with heart rate to form a corrected electromechanical time interval. In some examples, the control circuit 720 is configured to calculate the corrected time interval using a ratio that includes a measured cardiac depolarization interval (e.g., RR) and the time interval (e.g., EMT) between the mechanical cardiac event and the fiducial electrical cardiac event (e.g., $EMT_C=EMT/RR$). In certain examples, heart rate (HR) is used instead of depolarization interval to correct the electromechanical time interval (e.g., $EMT_C=(EMT)(HR)$). In some examples, the control circuit 720 establishes a baseline electromechanical time interval during normal sinus rhythm (NSR). To correct the monitored time interval, the control circuit 720 is configured to normalize a value of the electromechanical time interval measured during the episode of tachyarrhythmia with the baseline electromechanical time interval ($EMT_C=EMT/EMT_{BL}$). This normalization can account for changes in the time interval due to progression of chronic heart disease.

The control circuit 720 initiates anti-tachyarrhythmia therapy when the corrected electromechanical time interval satisfies a specified time interval threshold value during a detected episode of tachyarrhythmia and withholds anti-tachyarrhythmia therapy otherwise. In some examples, the control circuit establishes a baseline for the corrected time interval, and initiates anti-tachyarrhythmia therapy when detecting, during the episode of tachyarrhythmia, a change in the corrected time interval from the baseline time interval that satisfies a specified time interval change threshold.

Figure 8:
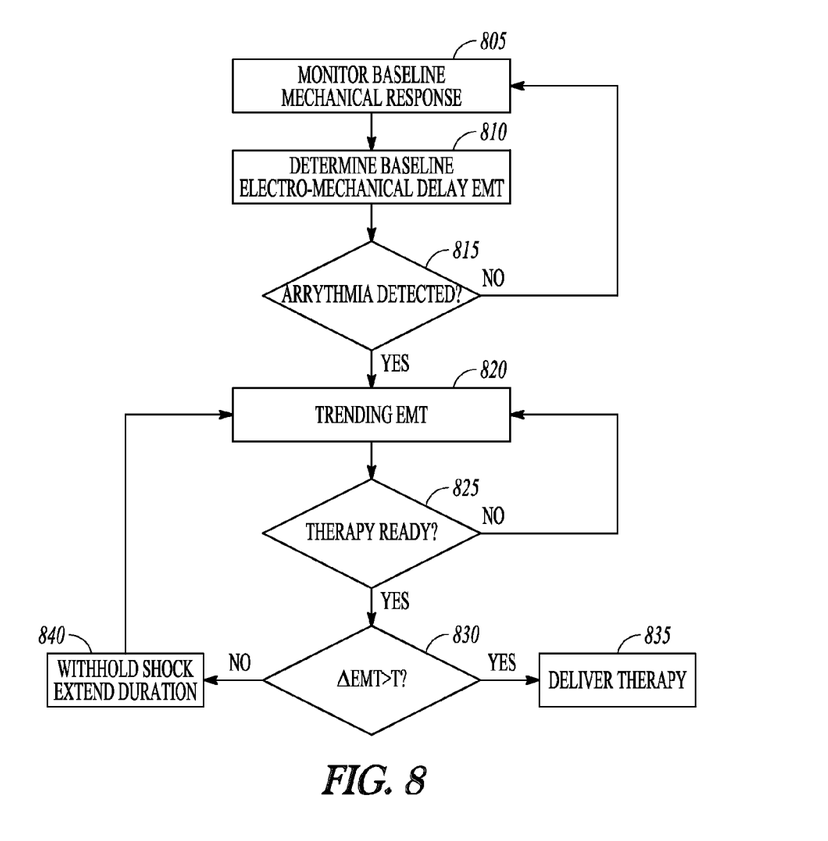
FIG. 8 shows an example of monitoring hemodynamic stability using a medical device.

FIG. 8 shows an example of monitoring hemodynamic stability using the medical device 700. At block 805, the device monitors the mechanical cardiac activity response to establish a baseline for the response. At block 810, the baseline of the electromechanical time interval or delay is determined. The device 700 may correct the delay for heart rate. At block 815, if an arrhythmia is not detected, the device 700 continues to monitor the baseline mechanical cardiac activity.

If arrhythmia is detected, the device 700 trends the electromechanical delay while the device prepares to deliver therapy (e.g., by charging one or more capacitors to deliver shock therapy) at block 825. At block 830, if the electromechanical delay exceeds a specified threshold (T), therapy is delivered at block 835. If the electromechanical delay does not exceed the specified threshold, therapy is withheld at block 840. The arrhythmia may have to be sustained for time duration in order to be declared a tachyarrhythmia. In some examples, the duration is extended at block 840 if the specified threshold is not satisfied.

As explained above, in some examples the therapy circuit 715 of FIG. 7 is configured to provide cardioversion/defibrillation shock therapy and ATP therapy. The control circuit 720 initiates cardioversion/defibrillation shock therapy when detecting a change in the time interval during the episode of tachyarrhythmia that satisfies the specified time interval change threshold, and withholds shock therapy and initiates ATP therapy when detecting a change in the time interval during the episode of tachyarrhythmia that does not satisfy the specified time interval change threshold.

According to some examples, multiple thresholds can be used. For example, the control circuit 720 may initiate anti-tachyarrhythmia pacing (ATP) therapy when the time interval satisfies a first specified time interval change threshold during the episode of tachyarrhythmia, initiate cardioversion/defibrillation shock therapy when the time interval satisfies a second specified time interval change threshold during the episode of tachyarrhythmia, and withhold both shock and ATP therapy otherwise.

The monitored electromechanical time interval can also be used to gauge the recovery to the hemodynamic system after therapy (ATP or shock) is delivered. Thus, the delay can be also monitored following the therapy to decide if additional therapy is needed. The timer circuit 735 monitors the electromechanical time interval after delivery of the anti-tachyarrhythmia therapy, and the control circuit can re-initiate the anti-tachyarrhythmia therapy when the corrected electromechanical time interval satisfies the same or a different time interval change threshold. For example, the time interval threshold value may be lowered for a specified time period after therapy is delivered.

In some examples, a parameter of the initiated therapy is adjusted according to the monitored time interval. ATP pacing typically includes one more bursts of pacing pulse to try and capture depolarization of the heart. Based on a measured value of the electromechanical time interval, the control circuit may change one or more ATP parameters, such as pacing pulse amplitude, number of pulses in a burst, and the number of bursts applied in the ATP, etc. For shock therapy, the amplitude of the shock may be adjusted based on a measured value of the electromechanical time interval. Further, the control circuit 720 may extend the detection duration used to detect tachyarrhythmia.

These several examples of devices and methods to detect tachyarrhythmia show that monitoring electromechanical cardiac delay can reduce unnecessary therapy, especially shock therapy, because such therapy is not delivered unless and until the therapy is deemed necessary. Providing shocks only unless and when such therapy is necessary contributes to a better outcome of device-based therapy for the patient.

ADDITIONAL NOTES AND EXAMPLES

Example 1 includes subject matter (such as an apparatus) comprising a cardiac signal sensing circuit configured to provide a cardiac signal representative of electrical cardiac activity, a physiologic sensor circuit configured to provide a physiologic sensor signal representative of mechanical cardiac activity, a therapy circuit configured to provide anti-tachyarrhythmia therapy, and a control circuit communicatively coupled to the cardiac signal sensing circuit, the physiologic sensor circuit, and the therapy circuit. The control circuit includes a cardiac depolarization detection circuit configured to detect a cardiac depolarization using at least one of the cardiac signal and the physiologic sensor signal, a tachyarrhythmia detection circuit, and a timer circuit configured to monitor a time interval between a mechanical cardiac event and a detected fiducial electrical cardiac event. The control circuit is configured to correct the monitored time interval for variation with heart rate to form a corrected electromechanical time interval, initiate anti-tachyarrhythmia therapy when the corrected electromechanical time interval satisfies a specified time interval threshold value during a detected episode of tachyarrhythmia, and withhold anti-tachyarrhythmia therapy otherwise.

In Example 2, the subject matter of Example 1 can optionally comprise a control circuit that can be configured to calculate a corrected time interval using a ratio that includes a measured cardiac depolarization interval and the time interval between the mechanical cardiac event and the fiducial electrical cardiac event.

In Example 3, the subject matter of one or any combination of Examples 1 and 2 can optionally comprise a control circuit that can be configured to establish a baseline electromechanical time interval during NSR, and normalize a value of the electromechanical time interval measured during the episode of tachyarrhythmia with the baseline electromechanical time interval.

In Example 4, the subject matter of one or any combination of Examples 1-3 can optionally comprise a therapy circuit that can be configured to provide cardioversion/defibrillation shock therapy and anti-tachyarrhythmia pacing (ATP) therapy, and the control circuit can optionally be configured to initiate cardioversion/defibrillation shock therapy when detecting a change in the time interval during the episode of tachyarrhythmia that satisfies the specified time interval change threshold, and initiate anti-tachyarrhythmia pacing (ATP) therapy when detecting a change in the time interval during the episode of tachyarrhythmia that does not satisfy the specified time interval change threshold.

In Example 5, the subject matter of one or any combination of Examples 1-3 can optionally comprise a therapy circuit that can be configured to provide cardioversion/defibrillation shock therapy and anti-tachyarrhythmia pacing (ATP) therapy, and the control circuit can optionally be configured to initiate anti-tachyarrhythmia pacing (ATP) therapy when the time interval satisfies a first time interval change threshold during the episode of tachyarrhythmia, and initiate cardioversion/defibrillation shock therapy when the time interval satisfies a second time interval change threshold during the episode of tachyarrhythmia.

In Example 6, the subject matter of one or any combination of Examples 1-5 can optionally comprise a control circuit that can be configured to establish a baseline for the corrected time interval between a mechanical cardiac event and a fiducial electrical cardiac event, and initiate anti-tachyarrhythmia therapy when detecting, during the episode of tachyarrhythmia, a change in the corrected time interval from the baseline time interval that satisfies a specified time interval change threshold.

In Example 7, the subject matter of one or any combination of Examples 1-6 can optionally comprise a timer circuit that can be configured to monitor the electromechanical time interval after delivery of the anti-tachyarrhythmia therapy, and the control circuit can optionally be configured to re-initiate the anti-tachyarrhythmia therapy when the corrected electromechanical time interval satisfies the same or a different time interval change threshold.

In Example 8, the subject matter of one or any combination of Examples 1-7 can optionally comprise a physiologic sensor circuit that can include a cardiac pressure sensing circuit and a timer circuit that can be configured to monitor a time interval between the detected fiducial electrical cardiac event and a detected fiducial in systolic pressure.

In Example 9, the subject matter of Example 8 can optionally comprise a cardiac pressure sensing circuit that can be configured (e.g., shaped and sized) for placement in or near at least one of the right ventricle, the left ventricle, and the pulmonary artery.

In Example 10, the subject matter of one or any combination of Examples 1-9 can optionally comprise a physiologic sensor circuit that can include a heart sound sensing circuit and a timer circuit that can be configured to monitor a time interval between the detected fiducial electrical cardiac event and a measurement of a detected heart sound.

In Example 11, the subject matter of one or any combination of Examples 1-10 can optionally comprise a physiologic sensor circuit that can include a cardiac impedance sensing circuit and a timer circuit that can be configured to monitor a time interval between the detected fiducial electrical cardiac event and a detected fiducial in cardiac impedance.

Example 12 can include subject matter, or can optionally by combined with the subject matter of one or any combination of Examples 1-11 to include subject matter (such as a method, a means for performing acts, or a machine-readable medium including instructions that, when performed by the machine, cause the machine to perform acts) comprising monitoring a time interval between a detected mechanical cardiac event and a detected fiducial electrical cardiac event, detecting an episode of tachyarrhythmia, correcting the monitored time interval for variation with heart rate to form a corrected electromechanical time interval, initiating anti-tachyarrhythmia therapy when the corrected electromechanical time interval satisfies a specified time interval threshold value during the episode of tachyarrhythmia, and withholding anti-tachyarrhythmia therapy otherwise.

Such subject matter can include a means for monitoring a time interval between a detected mechanical cardiac event and a detected fiducial electrical cardiac event, an illustrative example of which can include a timer circuit integral to or coupled to a control circuit. The control circuit can be an ASIC, processor, DSP, microprocessor, or other type of processor. Such subject matter can include means for detecting an episode of tachyarrhythmia, an illustrative example of which includes a tachyarrhythmia detection circuit of a control circuit. Such subject matter can include means for correcting the monitored time interval for variation with heart rate to form a corrected electromechanical time interval, an illustrative example of which is a control circuit. Such subject matter can include means for initiating anti-tachyarrhythmia therapy, an illustrative example of which is a control circuit communicatively coupled to a therapy circuit.

In Example 13, the subject matter of Example 12 can optionally comprise correcting the time interval that can include forming a ratio using the monitored time interval and one of a measured heart rate or a measured heart beat interval.

In Example 14, the subject matter of one or any combination of Examples 12 and 13 can optionally comprise correcting the time interval that can include determining a baseline electromechanical time interval during normal sinus rhythm (NSR) and normalizing a value of the electromechanical time interval measured during the episode of tachyarrhythmia with the baseline electromechanical time interval.

In Example 15, the subject matter of one or any combination of Examples 12-14 can optionally comprise initiating anti-tachyarrhythmia therapy that can include initiating cardioversion/defibrillation shock therapy when detecting, during the episode of tachyarrhythmia, a change in the time interval that satisfies the specified time interval change threshold, and initiating ATP therapy when detecting a change in the time interval during the episode of tachyarrhythmia that does not satisfy the specified time interval change threshold.

In Example 16, the subject matter of one or any combination of Examples 12-14 can optionally comprise initiating anti-tachyarrhythmia therapy that can include initiating ATP therapy when the time interval satisfies a first specified time interval change threshold during the episode of tachyarrhythmia, and initiating cardioversion/defibrillation shock therapy when the time interval satisfies a second specified time interval change threshold during the episode of tachyarrhythmia.

In Example 17, the subject matter of or any combination of Examples 12-16 can optionally include adjusting a parameter of the initiated therapy according to the monitored time interval.

In Example 18, the subject matter of one or any combination of Examples 12-17 can optionally comprise monitoring a time interval between the detected fiducial electrical cardiac event and a detected fiducial in at least one of a signal representative of cardiac impedance and a signal representative of right ventricular systolic pressure.

In Example 19, the subject matter of one or any combination of Examples 12-18 can optionally include monitoring a time interval between the detected fiducial electrical cardiac event and a detected fiducial of a heart sound signal.

In Example 20, the subject matter of one or any combination of Examples 12-19 optionally includes monitoring a time interval that can include monitoring a baseline time interval between the fiducial electrical cardiac event and a fiducial of the mechanical cardiac event, and the initiating anti-tachyarrhythmia therapy optionally includes initiating anti-tachyarrhythmia therapy when detecting, during the episode of tachyarrhythmia, a change in the time interval from the baseline time interval that satisfies a specified time interval change threshold.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." In the event of inconsistent usages between this document and any documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
  a cardiac signal sensing circuit configured to provide a cardiac signal representative of electrical cardiac activity;
  a physiologic sensor circuit configured to provide a physiologic sensor signal representative of right ventricular pressure;
  a therapy circuit configured to provide anti-tachyarrhythmia therapy; and
  a control circuit communicatively coupled to the cardiac signal sensing circuit, the physiologic sensor circuit, and the therapy circuit, wherein the control circuit includes:
    a cardiac depolarization detection circuit configured to detect a cardiac depolarization using at least one of the cardiac signal and the physiologic sensor signal;
    a tachyarrhythmia detection circuit; and
    a timer circuit configured to monitor an electromechanical time interval between a detected mechanical cardiac event and a detected fiducial electrical cardiac event, wherein the detected mechanical event includes peak right ventricular systolic pressure; and
    wherein the control circuit is configured to:
      determine a baseline for the electromechanical time interval;
      normalize the monitored time interval using the determined baseline to form a corrected electromechanical time interval;
      initiate anti-tachyarrhythmia therapy when the corrected electromechanical time interval satisfies a specified tachyarrhythmia detection time interval threshold value during a detected episode of tachyarrhythmia; and
      withhold anti-tachyarrhythmia therapy otherwise.

2. The apparatus of claim wherein the control circuit is configure to:
  establish the baseline electromechanical time interval during normal sinus (NSR); and
  normalize the value of the time interval between the mechanical cardiac event and fiducial electrical cardiac event measured during the episode of tachyarrhythmia.

3. The apparatus of claim 1,
  wherein the therapy circuit is configured to provide cardioversion/defibrillation shock therapy and anti-tachyarrhythmia pacing (ATP) therapy, and
  wherein the control circuit is configured to:
    initiate cardioversion/defibrillation shock therapy when detecting a change in the corrected electromechanical time interval during the episode of tachyarrhythmia that satisfies a specified tachyarrhythmia detection time interval change threshold; and
    initiate anti-tachyarrhythmia pacing (ATP) therapy when detecting a change in the corrected electromechanical time interval during the episode of tachyarrhythmia that does not satisfy the specified tachyarrhythmia detection time interval change threshold.

4. The apparatus of claim 1,
wherein the therapy circuit is configured to provide cardioversion/defibrillation shock therapy and anti-tachyarrhythmia pacing (ATP) therapy, and
wherein the control circuit is configured to:
initiate anti-tachyarrhythmia pacing (ATP) therapy when the corrected electromechanical time interval satisfies a first tachyarrhythmia detection time interval change threshold during the episode of tachyarrhythmia; and
initiate cardioversion/defibrillation shock therapy when the corrected electromechanical time interval satisfies a second tachyarrhythmia detection time interval change threshold during the episode of tachyarrhythmia.

5. The apparatus of claim 1, wherein the control circuit is configured to:
establish a baseline for the corrected electromechanical time interval between a mechanical cardiac event and a fiducial electrical cardiac event; and
initiate anti-tachyarrhythmia therapy when detecting, during the episode of tachyarrhythmia, a change in the corrected electromechanical time interval from the baseline time interval that satisfies a specified time interval change threshold.

6. The apparatus of claim 1,
wherein the timer circuit is configured to monitor the electromechanical time interval after delivery of the anti-tachyarrhythmia therapy; and
wherein the control circuit is configured to re-initiate the anti-tachyarrhythmia therapy when the corrected electromechanical time interval satisfies the same or a different time interval change threshold.

7. The apparatus of claim 1,
wherein the physiologic sensor circuit includes a cardiac pressure sensing circuit, and
wherein the timer circuit is configured to monitor a time interval between the detected fiducial electrical cardiac event and a detected fiducial in systolic pressure.

8. The apparatus of claim 7, wherein the cardiac pressure sensing circuit is configured for placement in or near the right ventricle.

9. The apparatus of claim 1,
including a heart sound sensing circuit, and
wherein the timer circuit is further configured to monitor a time interval between the detected fiducial electrical cardiac event and a measurement of a detected heart sound.

10. The apparatus of claim 1,
including a cardiac impedance sensing circuit, and
wherein the timer circuit is further configured to monitor a time interval between the detected fiducial electrical cardiac event and a detected fiducial in cardiac impedance.

* * * * *